(12) United States Patent
Watanabe et al.

(10) Patent No.: US 6,262,322 B1
(45) Date of Patent: Jul. 17, 2001

(54) ADSORBENT FOR AROMATIC ISOMERS AND PRODUCTION OF AROMATIC ISOMERS

(75) Inventors: Masatoshi Watanabe, Tajimi; Masahito Yoshikawa; Kazuyoshi Iwayama, both of Nagoya, all of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/434,891

(22) Filed: Nov. 5, 1999

(30) Foreign Application Priority Data

Nov. 20, 1998 (JP) .................................... 10-330515

(51) Int. Cl.$^7$ .................................................. C07C 17/38
(52) U.S. Cl. ............................................ 570/211; 570/179
(58) Field of Search ...................................... 570/211, 179

(56) References Cited

U.S. PATENT DOCUMENTS 4,774,371 * 9/1988 Miwa et al. .......................... 570/211

* cited by examiner

*Primary Examiner*—Alan Siegel
(74) *Attorney, Agent, or Firm*—Schnader Harrison Segal & Lewis LLP (57) ABSTRACT

An adsorbent which comprises a zeolite containing Cs and/or Rb, said zeolite being characterized by that the ratio of [the number of moles of Cs and/or R in the zeolite] to [the number of moles of Al in the zeolite] is 0.1 or less. This adsorbent permits efficient separation of an isomer from a mixture of aromatic isomers.

8 Claims, 4 Drawing Sheets

ADSORBENT FOR AROMATIC ISOMERS AND PRODUCTION OF AROMATIC ISOMERS

BACKGROUND OF THE INVENTION

1. Field of the Invention

The present invention relates to a process for producing aromatic isomers by adsorption separation and to an adsorbent used therefor.

2. Description of the Related Arts

As processes for separation of aromatic isomers, particularly halogenated aromatic isomers, rectification, cryogenic separation, and adsorption separation are known so far. The present invention relates to a process for adsorption separation.

Separation by rectification suffers the disadvantage of requiring a rectifying column with a large number of plates because halogenated aromatic isomers differ from one another only slightly in boiling point. Cryogenic separation suffers the disadvantage of requiring valuable equipment and high energy costs for cooling. In order to eliminate these disadvantages, processes for adsorption separation have been studied and developed. Japanese Patent Publication No. 5155/1962 discloses that an adsorbent prepared by introduction of alkali metal ions or alkaline earth metal ions into zeolite X can be used for separation of halogenated aromatic isomers. Japanese Patent Laid-Open No. 105434/1978 discloses a process for separation of specific isomers from a mixture of dichlorobenzene isomers by means of an adsorbent prepared by introduction of Cs or Rb ions into zeolite Y. Japanese Patent Laid-Open Nos. 31627/1982, 35528/1982, and 191933/1982 disclose a process for adsorption separation of chlorotoluene isomers by means of K ion-exchanged zeolite Y as an adsorbent. Japanese Patent Laid-Open Nos. 131923/1983 and 176223/1984 respectively disclose Ag ion- and K ion-exchanged zeolite Y and Na ion- and Cu ion-exchanged zeolite Y to be used as an adsorbent for separation of m-chlorotoluene.

These adsorbents permit separation of aromatic isomers but their performance is not satisfactory.

SUMMARY OF THE INVENTION

It is an object of the present invention to provide an adsorbent for selective separation of desired aromatic isomers from a mixture of aromatic isomers, particularly a mixture of hologenated aromatic isomers. It is another object of the present invention to provide a process for production of halogenated aromatic isomers by adsorption separation with the above adsorbent.

It is another object of the present invention to provide an adsorbent for separation of a meta-isomer from a mixture of dihalogenated aromatic isomers. It is another object of the present invention to provide a process for production of a meta-isomer by adsorption separation with said adsorbent.

The first aspect of the present invention resides in an adsorbent which comprises a zeolite containing Cs and/or Rb, the zeolite being characterized in that the ratio of [the number of moles of Cs and/or R in the zeolite] to [the number of moles of Al in the zeolite] is 0.1 or more.

The second aspect of the present invention resides in a process for production of halogenated aromatic isomers which comprises separation of at least one species of isomer from a mixture of aromatic isomers with the aid of an adsorbent which is a zeolite containing Cs and/or Rb, the zeolite being characterized in that the ratio of [the number of moles of Cs and/or R in the zeolite] to [the number of moles of Al in the zeolite] is 0.1 or more.

DESCRIPTION OF THE PREFERRED EMBODIMENTS

The adsorbent used in the present invention is a zeolite containing Cs and/or Rb, the zeolite being characterized in that the ratio of [the number of moles of Cs and/or R in the zeolite] to [the number of moles of Al in the zeolite] is 0.1 or more.

Zeolites usually refer to porous crystalline aluminosilicates. Zeolites used in the present invention may include crystalline metallosilicate in which aluminum is substituted by iron or gallium. Any metallosilicate is acceptable; but those capable of ion exchange are desirable and trivalent or divalent metal silicates are desirable. Zeolites used in the present invention are not specifically restricted; however, those having a pore inlet diameter larger than a ring of 12 oxygen atoms and having a multidimensional pore structure are desirable. Examples of such zeolites include β-type zeolite and faujasite-type zeolite, with the latter being preferable. Aluminosilicate is represented by the following formula:

$$0.9\pm0.2\ M_{2/n}O:Al_2O_3:xSiO_2:yH_2O$$

where, M denotes a cation and n denotes its valence. In the case of faujasite, x is usually in the range of from 2 to 6. Faujasite is classified as zeolite X if x is 2 to 3 and as zeolite Y if x is 3 to 6. Zeolite Y may become ultrastable zeolite (USY) upon dealuminization to have the value of x of 6 or more. Any of these zeolites may be used in the present invention. However, zeolite X and zeolite Y are preferable.

Zeolite X and zeolite Y may differ in performance for adsorption separation depending on the kind of halogenated aromatic isomers to be separated. For example, in the case of separation of m-chlorotoluene from a mixture of chlorotoluene isomers, zeolite Y would be desirable if m-chlorotoluene is a non-adsorptive component (or raffinate) and zeolite X would be desirable if m-chlorotoluene is an adsorptive component (or extract). Incidentally, the value of y varies depending on the degree of hydration.

The cation M in zeolite of faujasite-type usually includes sodium. This cation may be replaced by any other one by ion exchange. Cation exchange may be accomplished usually by bringing zeolite into contact with an aqueous solution of a compound containing the desired cation. Examples of such a compound include chlorides, nitrates, sulfates, carbonates, and hydroxides. The amount of ion exchange varies depending on the kind of cation; it may be established as desired according to the amount of cation in the aqueous solution and the number of ion exchange treatments. Ion exchange should be followed by thorough rinsing for removal of those ions (such as sodium ions, chlorine ions, and nitrate ions) which have been exchanged and dissolved in the aqueous solution.

The adsorbent used in the present invention should contain Cs and/or Rb as essential cations. These cations may not be at ion exchange sites so long as they are contained in zeolite. However, they should preferably be at ion exchange sites. The content of Cs and/or Rb should be such that [the number of moles of Cs and/or R in the zeolite] to [the number of moles of Al in the zeolite] is 0.1 or more, preferably 0.3 or more, particularly 0.5 or more. Such a specific content is necessary for efficient separation of halogenated aromatic isomers. The upper limit of ion exchange is usually equal to the number of moles of Al in zeolite. In other words, it is about 1.0. However, in the case of the adsorbent used in the present invention, the upper limit of ion exchange would be about 0.7 because not all Cs and/or Rb ions exchange with ions in zeolite X or Y because of their large ionic radius.

The content of Cs and/or Rb may be determined in any manner, such as atomic absorption spectrometry, fluorescent X-ray analysis, and energy dispersion X-ray analysis, which is capable of specifying the ratio of elements. To be concrete, elements contained in zeolite are traced and determined and the content of Cs and/or Rb is estimated. In the case of molded zeolite containing a binder, the content of Cs and/or Rb may be calculated by subtracting the content of aluminum in the binder (if the amount of the binder is known) or it may be replaced by the content of Cs and/or Rb in metals excluding Si and Al (if the amount of the binder is unclear). The kind of the metals that can coexist with Cs and Rb without adverse effect varies depending on the halogenated aromatic isomers to be separated. For example, the presence of K and/or Ag is desirable if m-chlorotoluene is to be separated as raffinate from a mixture of chlorotoluene isomers, or the presence of Pb and/or K (in addition to Cs and Rb) is desirable if m-dichlorobenzene is to be separated as raffinate from a mixture of dichlorobenzene isomers.

Adsorbents are usually used in the form of granules obtained by coagulating zeolite. Granulation may be accomplished with the aid of a binder such as alumina and clay. Granulation may be accomplished by mixing zeolite together with a binder, extruding the mixture through an extruder, and shaping the extrudate into spheres by using a Marumerizer. The particle size is usually larger than 0.1 mm. Particles smaller than 0.1 mm lead to an increase in pressure loss. The upper limit of the particle size is usually 5 mm. The adsorbent used in this present invention should preferably have a smaller particle size for efficient diffusion because it contains large cations such as Cs and Rb. The particle size should preferably be smaller than 1 mm, more preferably smaller than 0.5 mm.

Prior to use, the adsorbent should be heated usually at 200 to 600° C. to remove water almost completely from zeolite.

The adsorbent according to the present invention is used for adsorption separation of a specific isomer from a mixture of halogenated aromatic isomers, and this adsorption separation may be either chromatographic separation or separation by simulated moving bed. The latter is preferable when only one specific isomer is to be separated.

The continuous adsorption separation by a simulated moving bed basically consists of the cyclic steps of adsorption, concentration, desorption, and recovery of desorbent which are explained below.

(1) Adsorption: In this step, the feed stock containing a mixture of 2-substituted or 3-substituted aromatic isomers is brought into contact with the adsorbent of the present invention. Selective adsorption takes place according to the adsorptive strength of each component. The strongly adsorbed component is recovered as the extract component together with the desorbent as mentioned later.

(2) Concentration: The weakly adsorbed component is further brought into contact with the adsorbent, so that it is purified and recovered as the raffinate together with the desorbent.

(3) Desorption: The weakly adsorbed component, which has been highly purified, is recovered as the raffinate. At the same time, the strongly adsorbed component is expelled from the adsorbent by a desorbent and recovered as the extract component together with the desorbent.

(4) Recovery of adsorbent: The adsorbent, which has adsorbed substantially only the desorbent, is brought into contact with part of the raffinate flow, so that part of the desorbent contained in the adsorbent is recovered as the recovery flow of the desorbent.

Figure 1:
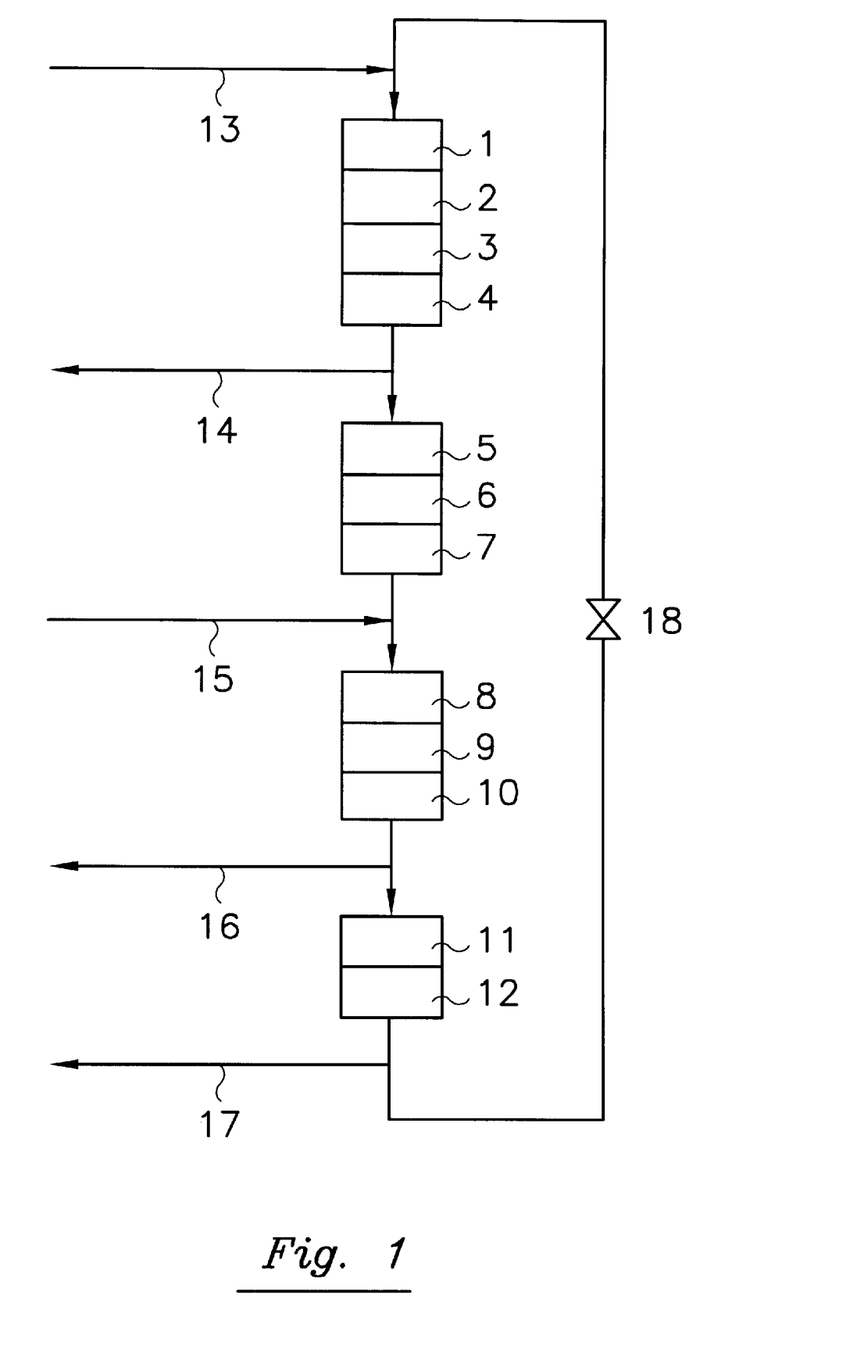
FIG. 1 is a schematic diagram showing the procedure for adsorption separation by a simulated moving bed, which is one embodiment according to the present invention.

FIG. 1 schematically shows the procedure for adsorption separation by a simulated moving bed. There are shown adsorbing chambers 1 to 12 filled with adsorbent, which are serially connected for circulation. There are also shown a desorbent feed line 13, an extract discharge line 14, an isomer mixture feed line 15, a raffinate discharge line 16, a desorbent recovery line 17, and a valve 18.

The isomers for adsorption separation according to the present invention are those of aromatic compounds, preferably halogenated aromatic compounds represented by the following formula.

(where X denotes a $C_{1-6}$ alkyl group or a halogen, and Y denotes a halogen.)

Examples of the halogenated aromatic compounds include chlorotoluene, dichlorobenzene, chloroethylbenzene, chloropropylbenzene, chlorocumene, and bromotoluene. The adsorbent of the present invention fully produces its effect when it is used for separation of chlorotoluene and dichlorobenzene isomers.

The desorbent employed for the above-mentioned procedure of adsorption separation is not specifically restricted; it includes, for example, alkyl-substituted aromatic hydrocarbons, halogenated aromatic hydrocarbons, and halogenated alkyl-substituted aromatic hydrocarbons.

Examples of the alkyl-substituted aromatic hydrocarbons include toluene, ethylbenzene, xylene, propylbenzene, butylbenzene, trimethylbenzene, diethylbenzene, and tetramethylbenzene.

Examples of the halogenated aromatic hydrocarbons include chlorobenzene, dichlorobenzene, and trichlorobenzene.

Examples of the halogenated alkyl-substituted aromatic hydrocarbons include chlorotoluene, dichlorotoluene, and chloroxylene.

These desorbents may be used alone or in combination with one another. An adequate desorbent should be selected according to the substance to be separated. If disubstituted halogenated aromatic compounds are to be separated into m-form (as the raffinate component), for example if chlorotoluene isomers are to be separated into m-chlorotoluene or if dichlorobenzene isomers are to be separated into m-dichlorobenzene, an adequate desorbent is a halogen-free aromatic compound, preferably alkyl-substituted aromatic compound, such as xylene, particularly m-xylene. If disubstituted halogenated aromatic compounds are to be separated into m-form (as the extract component), an adequate desorbent is xylene, particularly p-xylene.

The conditions for adsorption separation are not specifically restricted. The temperature is usually in the range of from room temperature to 350° C., preferably from 50 to 250° C. The pressure is usually in the range of from atmospheric pressure to 20 MPa, preferably from atmospheric pressure to 3 MPa. The procedure for adsorption separation according to the present invention may be accomplished in gas phase; however, it should preferably be carried out in liquid phase so as to reduce undesirable side reactions of feedstock or desorbent by keeping the operating temperature low.

The term "procedure for adsorption separation" as used in the present invention means not only "separation" but it also production of specific substances by adsorption separation.

EXAMPLES

The invention will be described with reference to the following examples. In examples, the adsorbing characteristics of the adsorbent are expressed by the adsorption selectivity α defined by the equations below.

$$\alpha\, p/m = \frac{\left(\frac{\text{Fraction by weight of } p}{\text{Fraction by weight of } m}\right)_A}{\left(\frac{\text{Fraction by weight of } p}{\text{Fraction by weight of } m}\right)_U}$$

$$\alpha\, o/m = \frac{\left(\frac{\text{Fraction by weight of } o}{\text{Fraction by weight of } m}\right)_A}{\left(\frac{\text{Fraction by weight of } o}{\text{Fraction by weight of } m}\right)_U}$$

(where o, m, and p each represents the o-isomer, m-isomer, and p-isomer of disubstituted aromatic isomers; and A denotes the adsorpt ion phase and U denotes the liquid phase in equilibrium with the adsorption phase.) These equations suggest that as the value of α becomes larger than 1, m-isomer becomes less prone to adsorption than o-isomer and p-isomer, and that as the value of α becomes smaller than 1, m-isomer becomes more prone to adsorption than o-isomer and p-isomer.

For n-isomer to be separated as the raffinate component (unadsorbed component), it is necessary that the values of both α o/m and α p/m should be greater than 1, preferably 1.4 or more from the standpoint of separation efficiency. For m-isomer to be separated as the extract component (adsorbed component), it is necessary that the values of both α o/m and α p/m should be smaller than 1, preferably 0.7 or less from the standpoint of separation efficiency.

"[number of moles of Cs and/or Rb in zeolite]/[number of moles of Al in zeolite]" indicates the content of Cs and/or Rb which are determined by energy dispersion X-ray analysis.

Preparation of Adsorbents

Adsorbent 1

Sodium-type zeolite X (Na-X for short hereinafter). 100 pbw of "ZeolumF-9" powder (from Tosoh Corporation) is mixed with 25 pbw (in terms of alumina) of alumina sol as a binder (#200, $Al_2O_3$=10 wt %, from Nissan Chemical Industries, Ltd.). The resulting mixture is made into granules, 0.15 to 0.5 mm in particle size. The Na-X zeolite in granular form is dried at 120° C. and then calcined at 500° C. The content of Cs is 0.

Adsorbent 2

Sodium-type zeolite Y (Na-Y for short hereinafter). 100 pbw of "Zeolum Na-5.1" powder (from Tosoh Corporation) is mixed with 15 pbw (in terms of alumina) of alumina sol as a binder (#200, $Al_2O_3$=10 wt %, from Nissan Chemical Industries, Ltd.) The resulting mixture is made into granules, 0.15 to 0.5 mm in particle size. The Na-Y zeolite in granular form is dried at 120° C. and then calcined at 500° C. The content of Cs is 0.

Adsorbent 3

10 g of adsorbent 1 is immersed in a solution of cesium nitrate (7.94 g) dissolved in 40 cc of pure water at 80° C. for 1 hour. The treated adsorbent is filtered off, rinsed thoroughly, and finally dried. The content of Cs is 0.4.

Adsorbent 4

10 g of adsorbent 1 is immersed in a solution of rubidium nitrate (3.00 g) dissolved in 40 cc of pure water at 80° C. for 1 hour. The treated adsorbent is filtered off, rinsed thoroughly, and finally dried. The content of Rb is 0.2.

Adsorbent 5

10 g of adsorbent 2 is immersed in a solution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off and rinsed thoroughly. The adsorbent is further immersed in a solution of cesium nitrate (7.21 g) dissolved in 40 cc of pure water at 80° C. for 1 hour. This procedure is repeated twice (in total) using freshly prepared cesium nitrate solution. The treated adsorbent is filtered off, rinsed thoroughly, and finally dried. The content of Cs is 0.5.

Adsorbent 6

10 g of adsorbent 2 is immersed in a solution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off and rinsed thoroughly. The adsorbent is further immersed in a solution of silver nitrate (1.26 g) dissolved in 40 cc of pure water at 80° C. for 1 hour. The treated adsorbent is filtered off. This procedure is repeated twice (in total) using freshly prepared silver nitrate solution. The treated adsorbent is filtered off and rinsed thoroughly. The adsorbent is further immersed in a solution of cesium nitrate (7.21 g) dissolved in 40 cc of pure water at 80° C. for 1 hour. This procedure is repeated twice (in total) using freshly prepared cesium nitrate solution. The treated adsorbent is filtered off, rinsed thoroughly, and finally dried. The content of Cs is 0.5.

Adsorbent 7

10 g of adsorbent 2 is immersed in a sdlution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off and rinsed thoroughly. The adsorbent is further immersed in a solution of silver nitrate (1.26 g) dissolved in 40 cc of pure water at 80° C. for 1 hour. The treated adsorbent is filtered off. This procedure is repeated twice (in total) using freshly prepared silver nitrate solution. The treated adsorbent is filtered off and rinsed thoroughly. The adsorbent is further immersed in a solution of cesium nitrate (2.88 g) dissolved in 40 cc of pure water at 80° C. for 1 hour. The treated adsorbent is filtered off, rinsed thoroughly, and finally dried. The content of Cs is 0.3.

Adsorbent 8

The same procedure as for adsorbent 7 is repeated except that the amount of cesium nitrate is changed to 1.44 g. The content of Cs is 0.1.

Adsorbent 9

The same procedure as for adsorbent 7 is repeated except that the amount of cesium nitrate is changed to 0.72 g. The content of Cs is 0.05.

Adsorbent 10

10 g of adsorbent 2 is immersed in a solution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off and rinsed thoroughly. The adsorbent is further immersed in a solution of silver nitrate (1.26 g) dissolved in 40 cc of pure water at 80° C. for 1 hour. The treated adsorbent is filtered off. This procedure is repeated twice (in total) using freshly prepared silver nitrate solution. The treated adsorbent is filtered off, rinsed thoroughly, and finally dried. The content of Cs is 0.

Adsorbent 11

10 g of adsorbent 2 is immersed in a solution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off and rinsed thoroughly. The adsorbent is further immersed in a solution of silver nitrate (1.26 g) dissolved in 40 cc of pure water at 80° C. for 1 hour. The treated adsorbent is filtered off. This procedure is repeated twice (in total) using freshly prepared silver nitrate solution. The treated adsorbent is filtered off and rinsed thoroughly. The adsorbent is further immersed in a solution of rubidium nitrate (5.45 g) dissolved in 40 cc of pure water at 80° C. for 1 hour. The treated adsorbent is filtered off. This procedure is repeated twice (in total) using freshly prepared rubidium nitrate solution. The treated adsorbent is filtered off, rinsed thoroughly, and finally dried. The content of Rb is 0.4.

Adsorbent 12

10 g of adsorbent 2 is immersed in a solution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off, rinsed thoroughly, and finally dried. The content of Cs is 0.

Adsorbent 13

10 g of adsorbent 2 is immersed in a solution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off and rinsed thoroughly. The adsorbent is further immersed in a solution of lead nitrate (2.45 g) dissolved in 40 cc of pure water at 80° C. for 1 hour. The treated adsorbent is filtered off and rinsed thoroughly. The adsorbent is further immersed in a solution of cesium nitrate (7.21 g) dissolved in 40 cc of pure water at 800 C for 1 hour. The treated adsorbent is filtered off: This procedure is repeated twice (in total) using freshly prepared cesium nitrate solution. The treated adsorbent is filtered off, rinsed thoroughly, and finally dried. The content of Cs is 0.5.

Adsorbent 14

10 g of adsorbent 2 is immersed in a solution of potassium nitrate (4.0 g) dissolved in 40 cc of pure water at 80° C. for 1 hour. The treated adsorbent is filtered off. This procedure is repeated eight times (in total) using freshly prepared potassium nitrate solution. The treated adsorbent is filtered off and rinsed thoroughly. The adsorbent is further immersed in a solution of lead nitrate (2.45 g) dissolved in 40 cc of pure water at 80° C. for 1 hour. The treated adsorbent is filtered off, rinsed thoroughly, and finally dried. The content of Cs is 0.

ADSORPTION EXPERIMENTS

EXAMPLES 1 AND 2 AND COMPARATIVE EXAMPLE 1

Adsorbents 3 and 4 were examined for adsorption selectivity in the adsorption of chlorotoluene isomers which employs p-xylene as a desorbent. The procedure is as follows. An autoclave (6 ml internal volume) is filled with 2.6 g of liquid phase mixture and 2.4 g of the adsorbent (calcined at 500° C.). The autoclave is allowed to stand at 130° C. f or 1 hour, with occasional stirring. The liquid phase mixture is composed of n-nonane, desorbent (p-xylene), and chlorotoluene (o:m:p=39.2:40.2:20.6) in a ratio of 5:50:50 (by weight). n-nonane is added as an internal standard substance for gas chromatography. It is substantially inactive in this experiment for adsorption.

The liquid phase mixture which has been in contact with the adsorbent is analyzed for its composition by gas chromatography. The adsorption selectivity for chlorotoluene isomersiscalculatedfromequation(1). Theresultsareshown in Table 1. It is apparent from Table 1 that the adsorbent of zeolite X containing Cs or Rb can separate m-chlorotoluene (as the strongly adsorbed component or the extract component) from a mixture of chlorotoluene isomers.

TABLE 1

|  | Adsorbent | Desorbent | α p/m | α o/m |
|---|---|---|---|---|
| Example 1 | Adsorbent 3 | p-xylene | 0.67 | 0.67 |
| Example 2 | Adsorbent 4 | p-xylene | 0.63 | 0.71 |
| Comparative Example 1 | Adsorbent 1 | p-xylene | 0.65 | 0.99 |

EXAMPLES 3 TO 7 AND COMPARATIVE EXAMPLES 2 AND 3

The same procedure as in Examples 1 and 2 was repeated except that the absorbent was replaced by adsorbents 5 to 11 which were calcined at 500° C. and the desorbent was replaced by m-xylene. The results are shown in Table 2. It is apparent from Table 2 that the adsorbent of zeolite Y containing Cs or Rb can separate m-chlorotoluene (as the weakly adsorbed component or the raffinate component) from a mixture of chlorotoluene isomers. It is also noted that the adsorption selectivity of α o/m is low if the content of Cs is 0.05 or less.

TABLE 2

|  | Adsorbent | Desorbent | α p/m | α o/m |
|---|---|---|---|---|
| Example 3 | Adsorbent 5 | m-xylene | 1.80 | 1.47 |
| Example 4 | Adsorbent 6 | m-xylene | 1.65 | 1.66 |
| Example 5 | Adsorbent 7 | m-xylene | 1.98 | 1.48 |
| Example 6 | Adsorbent 8 | m-xylene | 2.03 | 1.45 |
| Comparative Example 2 | Adsorbent 9 | m-xylene | 2.09 | 1.33 |
| Comparative Example 3 | Adsorbent 10 | m-xylene | 2.14 | 1.30 |
| Example 7 | Adsorbent 11 | m-xylene | 2.01 | 1.55 |

COMPARATIVE EXAMPLES 4 AND 5

The same procedure as in Examples 1 and 2 was repeated except that the absorbent was replaced by adsorbents 10 and 12 which were calcined at 500° C. and the desorbent was replaced by m-xylene or 3,4-dichlorotoluene. The results are shown in Table 3.

TABLE 3

|  | Adsorbent | Desorbent | α p/m | α o/m |
|---|---|---|---|---|
| Comparative Example 3 | Adsorbent 10 | m-xylene | 2.14 | 1.30 |
| Comparative Example 4 | Adsorbent 10 | 34-dichlorotoluene | 1.31 | 1.44 |
| Comparative Example 5 | Adsorbent 12 | m-xylene | 2.17 | 1.18 |

EXAMPLES 8 TO 9

The same procedure as in Examples 1 and 2 was repeated except that the absorbent was replaced by adsorbent 6 which was calcined at 500° C. and the desorbent was changed. The results are shown in Table 4. It is apparent from Table 4 that xylene is desirable as the desorbent and m-Xylene is particularly desirable as the desorbent to separate m-chlorotoluene as the raffinate component.

TABLE 4

|  | Adsorbent | Desorbent | α p/m | α o/m |
|---|---|---|---|---|
| Example 4 | Adsorbent 6 | m-xylene | 1.65 | 1.66 |
| Example 8 | Adsorbent 6 | o-xylene | 1.55 | 1.50 |
| Example 9 | Adsorbent 6 | 3,4-dichlorotoluene | 1.40 | 1.25 |

EXAMPLE 10

A stainless steel column, 1 m long and 4.6 mm in inside diameter, is filled with adsorbent 6 which was calcined at 500° C. The filledcolumn is placed in an oil bath at 130° C., and m-xylene as the desorbent is passed through it at a constant flow rate of 1.5 ml/min (at room temperature). Into the column is introduced a mixture of chlorotoluene (CT) (o:m:p=39.2:40.2:20.6) and n-nonane (n-C9) in a ratio of 100:5 (by weight). Then-nonane is addedas astandardforelutiontime. Its adsorption relative to other components is practically negligible. The eluate from the column outlet is sampled at constant intervals for analysis by gas chromatography. An elution curve as shown in FIG. 2 is obtained.

COMPARATIVE EXAMPLE 6

Figure 3:
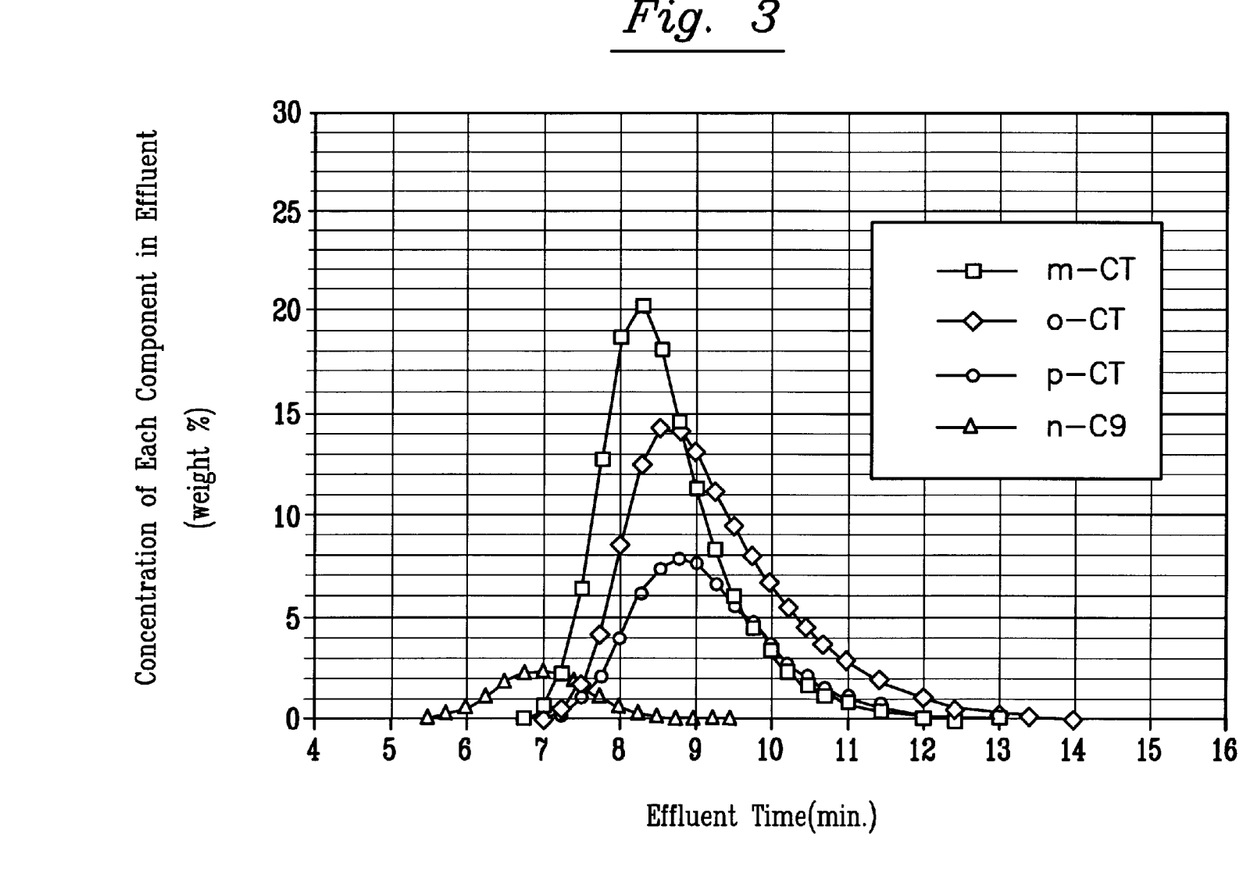
FIG. 3 is a diagram showing the change with time of the amount of effluent of each component in Comparative Example 6.

The same procedure as in Example 11 was repeated except that adsorbent 10 which was calcined at 500° C. was used and 3,4-dichlorotoluene was used as the desorbent. The elution curve is shown in FIG. 3.

Figure 2:
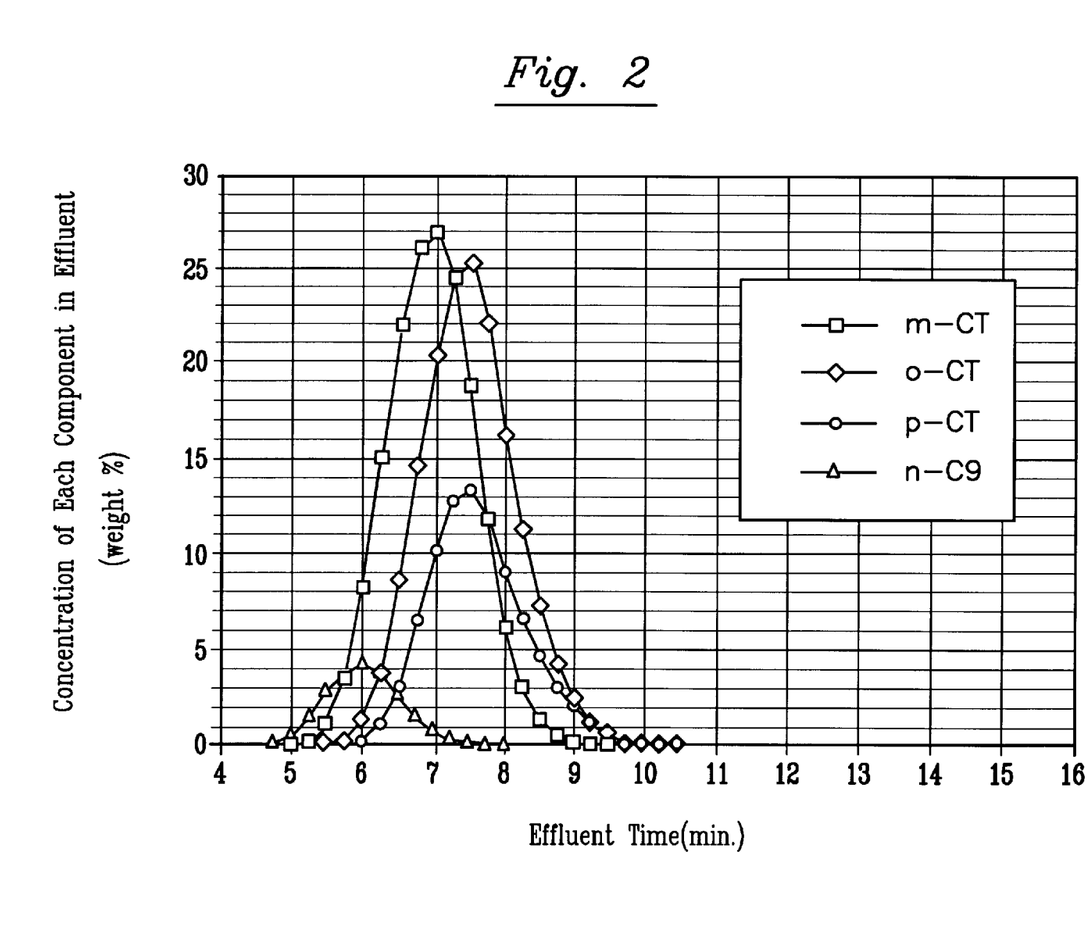
FIG. 2 is a diagram showing the change with time of the amount of effluent of each component in Example 10 of the present invention.

FIGS. 1 and 2 showing the peaks of respective components indicate that the zeolite Y containing Cs, Ag, and K, when used as an adsorbent in combination with m-xylene as a desorbent, permits efficient separation of m-chlorotoluene as the non-adsorbed component.

EXAMPLE 11

Adsorbent 13 was examined for adsorption selectivity in the adsorption of dichlorobenzene isomers which employs m-xylene as a desorbent. The procedure is as follows. An autoclave (6 ml internal volume) is filled with 2.6 g of liquid phase mixture and 2.5 g of the adsorbent (calcined at 500° C.). The autoclave is allowed to stand at 130° C. for 1 hour, with occasional stirring. The liquid phase mixture is composed of n-nonane, desorbent (m-xylene), and dichlorobenzene (o:m:p=39.6:40.0:20.4) in a ratio of 5:50:50 (by weight). n-nonane is added as an internal standard substance for gas chromatography. It is substantially inactive in this experiment for adsorption.

The liquid phase mixture which has been in contact with the adsorbent is analyzed for its composition by gas chromatography. The adsorption selectivity for dichlorobenzene isomers is calculated from equation (1). The results are shown in Table 5.

TABLE 5

|  | Adsorbent | Desorbent | α p/m | α o/m |
|---|---|---|---|---|
| Example 11 | Adsorbent 13 | m-xylene | 2.14 | 2.70 |

COMPARATIVE EXAMPLES 7 AND 8

The same procedure as in Example 12 was repeated except that the absorbent was replaced by adsorbent 14 which was calcined at 500° C. and the desorbent was replaced by m-xylene and 3,4-dichlorotoluene. The results are shown in Table 6.

TABLE 6

|  | Adsorbent | Desorbent | α p/m | α o/m |
|---|---|---|---|---|
| Comparative Example 7 | Adsorbent 14 | m-xylene | 1.66 | 2.37 |
| Comparative Example 8 | Adsorbent 14 | 3,4-dichlorotoluene | 1.75 | 2.00 |

EXAMPLE 12

Figure 4:
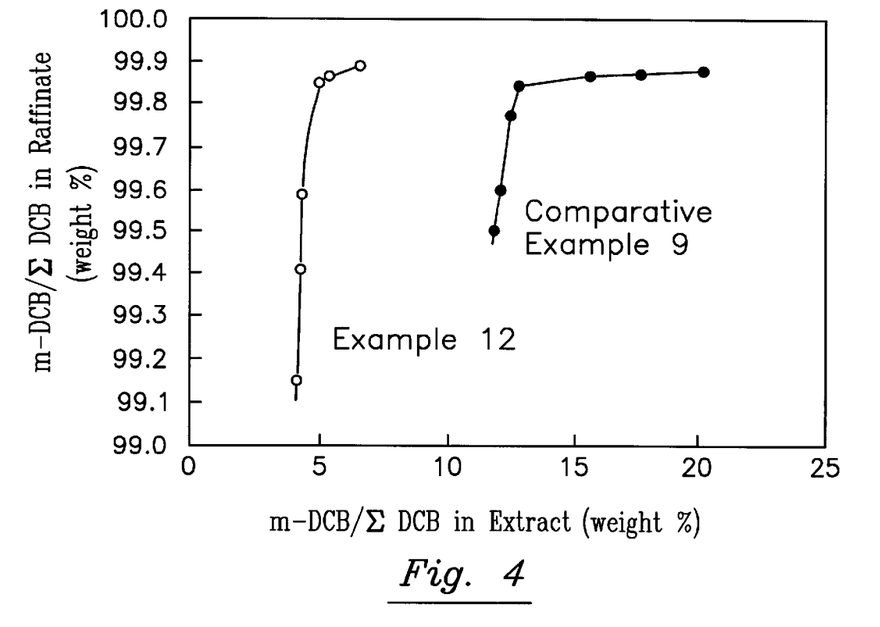
FIG. 4 is a diagram showing adsorption separation of dichlorobenzene isomers in Example 12 and Comparative Example 9.

Twelve columns (4.6 mm in diameter and 1 m long) were filled with about 160 g of adsorbent 13 which was calcined at 500° C. These twelve columns were used to the simulated moving bed process, four as the desorbing zone, three as the concentrating zone, three as the adsorbing zone, and two as the desorbent recovering zone. They were tested for ability to adsorb and separate a mixture of dichlorobenzene (DCB) isomers. The mixture of dichlorobenzene isomers as the feedstock has the composition of o:m:p=38:41:21. m-Xylene was used as a desorbent. The procedure was carried out at 120° C. The performance curve is shown in FIG. 4.

COMPARATIVE EXAMPLE 9

Twelve columns (4.6 mm in diameter and 1 m long) were filled with about 145 g of adsorbent 14 which was calcined at 500° C. These twelve columns were used to the simulated moving bed process, four as the desorbing zone, three as the concentrating zone, three as the adsorbing zone, and two as the desorbent recovering zone. They were tested f or ability to adsorb and separate a mixture of dichlorobenzene isomers. The mixture of dichlorobenzene isomers as the feedstock has the composition of o:m:p=38:41:21. 3,4-Dichlorotoluene was used as a desorbent. The procedure was carried out at 120° C. The performance curve is shown in FIG. 4.

In Example 12 and Comparative Example 9, m-isomer is the non-adsorbed component and hence is recovered as the raffinate component. The performance curve FIG. 4 indicates that the performance of separation is good when the concentration of m-isomer is low in the extract and the concentration of m-isomer is high in the raffinate. It has been shown that the adsorbent of the present invention, when used in combination with a specific desorbent, permits efficient separation of m-isomer from a mixture of dichlorobenzene isomers.

What is claimed is:

1. A process for production of aromatic isomers which comprises separation of at least one species of isomer from a mixture of halogenated aromatic isomers using an adsorbent which is a zeolite containing Cs and/or Rb, said zeolite being characterized in that the ratio of (the number of moles of Cs and/or Rb in the zeolite) to (the number of moles of Al in the zeolite) is 0.1 or more, wherein the halogenated aromatic isomer is a disubstituted halogenated aromatic isomer represented by the following formula:

(where X denotes a $C_{1-6}$ alkyl group or a halogen, and Y denotes a halogen.).

2. A process for production of halogenated aromatic isomers as defined in claim 1, wherein the disubstituted halogenated aromatic isomer is chlorotoluene or dichlorobenzene.

3. A process for production of aromatic isomers as defined in claims 1 or 2, which employs a desorbent composed mainly of a halogen-free aromatic compound.

4. A process for production of aromatic isomers as defined in claim 3, wherein the desorbent is composed mainly of xylene.

5. A process for production of aromatic isomers as defined in claim 1, wherein the zeolite is zeolite Y and the desorbent is one which is composed mainly of m-xylene, and m-isomer is separated as the raffinate component from a mixture of disubstituted halogenated aromatic isomers.

6. A process for production of aromatic isomers as defined in claim 1, wherein the zeolite is zeolite Y and the desorbent is one which is composed mainly of p-xylene, and m-isomer is separated as the extract component from a mixture of disubstituted halogenated aromatic isomers.

7. A process for production of aromatic isomers as defined in claim 1, wherein the zeolite is zeolite Y, the adsorbent is one which contains K and/or Ag, and the desorbent is one which is composed mainly of m-xylene, and m-chlorotoluene is separated as the raffinate component from a mixture of chlorotoluene isomers.

8. A process for production of halogenated aromatic isomers as defined in claim 1, wherein the zeolite is zeolite Y, the adsorbent is one which contains K and/or Pb, and the desorbent is one which is composed mainly of m-xylene, and m-dichlorobenzene is separated as the raffinate component from a mixture of dichlorobenzene isomers.

* * * * *

UNITED STATES PATENT AND TRADEMARK OFFICE
CERTIFICATE OF CORRECTION

PATENT NO. : 6,262,322 B1
DATED : July 17, 2001
INVENTOR(S) : Watanabe et al.

It is certified that error appears in the above-identified patent and that said Letters Patent is hereby corrected as shown below:

Column 5,
Line 47, please change "n-isomer" to -- m-isomer --.

Column 9,
Lines 41 and 42, please change "addedas astandardforelutiontime" to -- added as a standard for elution time --.

Signed and Sealed this

Twentieth Day of November, 2001

Attest:

NICHOLAS P. GODICI
Attesting Officer
Acting Director of the United States Patent and Trademark Office